US009892236B2

(12) United States Patent
Horwitz et al.

(10) Patent No.: US 9,892,236 B2
(45) Date of Patent: Feb. 13, 2018

(54) AUTOMATED METHOD OF GENERATING RECONCILIATION REPORTS REGARDING MISMATCHES OF CLINICAL DATA RECEIVED FROM MULTIPLE SOURCES DURING A CLINICAL TRIAL

(75) Inventors: Allan D. Horwitz, Philadelphia, PA (US); David L. Maslow, Philadelphia, PA (US)

(73) Assignee: Numoda Technologies, Inc., Philadelphia, PA (US)

( * ) Notice: Subject to any disclaimer, the term of this patent is extended or adjusted under 35 U.S.C. 154(b) by 581 days.

(21) Appl. No.: 13/053,726

(22) Filed: Mar. 22, 2011

(65) Prior Publication Data
US 2012/0246149 A1    Sep. 27, 2012

(51) Int. Cl.
| | |
|---|---|
| *G06F 7/00* | (2006.01) |
| *G06F 17/30* | (2006.01) |
| *G06F 19/00* | (2011.01) |
| *G06Q 10/10* | (2012.01) |
| *G06Q 50/24* | (2012.01) |

(52) U.S. Cl.
CPC .......... *G06F 19/363* (2013.01); *G06Q 10/10* (2013.01); *G06Q 50/24* (2013.01)

(58) Field of Classification Search
None
See application file for complete search history.

(56) References Cited

U.S. PATENT DOCUMENTS

| | | |
|---|---|---|
| 7,657,446 B1 | 2/2010 | Houriet, Jr. et al. |
| 2005/0071194 A1* | 3/2005 | Bormann et al. ................. 705/2 |
| 2007/0067189 A1* | 3/2007 | Boris et al. ....................... 705/3 |
| 2008/0003592 A1* | 1/2008 | Novakoff .......................... 435/6 |
| 2008/0046469 A1* | 2/2008 | Ikeguchi et al. ............ 707/104.1 |
| 2008/0147436 A1* | 6/2008 | Ohlsson ............................ 705/2 |
| 2008/0167533 A1* | 7/2008 | Leyendecker et al. ........ 600/300 |
| 2008/0270181 A1* | 10/2008 | Rosenberg ........................ 705/2 |
| 2009/0228303 A1* | 9/2009 | Faulkner et al. ................. 705/3 |
| 2009/0292554 A1* | 11/2009 | Schultz ............................. 705/2 |
| 2010/0049548 A1* | 2/2010 | Kubota ............................. 705/3 |
| 2010/0094836 A1* | 4/2010 | Duncan et al. ............... 707/705 |
| 2010/0191546 A1* | 7/2010 | Kanamarlapudi et al. ....... 705/3 |
| 2010/0198618 A1* | 8/2010 | Oliver et al. ..................... 705/3 |
| 2011/0313782 A1 | 12/2011 | DeMeyer et al. |

* cited by examiner

*Primary Examiner* — Tuan A Pham
(74) *Attorney, Agent, or Firm* — Panitch Schwarze Belisario & Nadel LLP

(57) ABSTRACT

An automated method is provided of generating a report of data collected from multiple sources during a clinical trial. The data includes a plurality of different data fields. A plurality of patients participate in the clinical trial. A first set of data obtained from case report forms associated with the patients is received at a processor. The case report forms are one source of data. A second set of data obtained from at least one source other than the case report forms is also received at the processor. At least some of the data in the first and second set of data include data associated with the same data fields. The processor identifies any mismatches in data associated with the same data fields in the first and second set of data. Mismatches associated with data fields obtained from the same case report forms are electronically grouped. A report is then generated of the data. The report shows the status of mismatches for each case report form or type of case report form.

22 Claims, 18 Drawing Sheets

START

↓ receive at a processor a first set of data obtained
from case report forms associated with the patients

↓ receive at the processor a second set of data obtained
from at least one source other than the case report forms

↓ identify, using the processor, any mismatches in data
associated with the same data fields in the first and second set of data

↓ electronically group, using the processor, mismatches associated
with data fields obtained from the same case report forms

↓ generate a report of the data that shows the status of mismatches
for each case report form or type of case report form

↓

END

Figure 1

START

↓ receive at a processor a first set of data obtained
from case report forms associated with the patients

↓ receive at the processor a second set of data obtained
from at least one source other than the case report forms

↓ identify, using the processor in conjunction with human determination,
any mismatches in data associated with the same data fields in the
first and second set of data that require reconciliation

↓ electronically store a field indication of the identified mismatches
that have had an action taken to address the mismatch

↓ generate a report of the collected data using the stored field indication
that includes the number of identified mismatches that require reconciliation,
and the number of identified mismatches that have had an action taken to
address the mismatch.

↓

END

Data Received
LAB1:  Monday, 22 March 2010 11:54 AM
LAB2:  Thursday, 06 May 2010 02:00 PM
LAB3:  Thursday, 08 April 2010 11:22 AM

Figure 10

| eCRF Name | Mismatches | Matches | All | Actions Taken | Tasks | Inactive |
|---|---|---|---|---|---|---|
| Informed Consent/Demographics | 13 | 95 | 108 | 1 | 6 | 0 |
| HIV Test | 16 | 56 | 72 | 0 | 10 | 0 |
| HLA Typing Sample | 53 | 57 | 110 | 0 | 21 | 0 |
| Biopsy | 38 | 34 | 72 | 0 | 33 | 0 |
| LEEP | 12 | 0 | 12 | 0 | 3 | 0 |
| HPV Testing | 105 | 65 | 170 | 0 | 31 | 0 |
| Serum Cytokine Analysis | 127 | 143 | 270 | 0 | 17 | 0 |
| Lab Collections | 94 | 286 | 380 | 17 | 17 | 1 |
| Totals: | 458 | 736 | 1194 | 18 | 138 | 1 |

Figure 11

| Patient ID | Status | eCRF Name | Mismatches | Matches | Actions Taken | Inactive |
|---|---|---|---|---|---|---|
| 101001 | LP | Informed Consent/Demographics | 0 | 3 | 0 | 0 |
| 101001 | LP | HIV Test | 0 | 2 | 0 | 0 |
| 101001 | LP | HLA Typing Sample | 2 † | 2 | 0 | 0 |
| 101001 | LP | Biopsy | 1 † | 1 | 0 | 0 |
| 101001 | LP | LEEP | 4 † | 0 | 0 | 0 |
| 101001 | LP | HPV Testing | 9 † | 5 | 0 | 0 |
| 101001 | LP | Serum Cytokine Analysis | 12 † | 12 | 0 | 0 |
| 101001 | LP | Lab Collections | 8 † | 20 | 0 | 0 |
| 101002 | LP | Informed Consent/Demographics | 1 † | 2 | 0 | 0 |
| 101002 | LP | HIV Test | 0 | 2 | 0 | 0 |
| 101002 | LP | HLA Typing Sample | 4 † | 2 | 0 | 0 |
| 101002 | LP | Biopsy | 1 † | 1 | 0 | 0 |
| 101002 | LP | LEEP | 4 † | 0 | 0 | 0 |
| 101002 | LP | HPV Testing | 9 † | 5 | 0 | 0 |
| 101002 | LP | Serum Cytokine Analysis | 18 † | 12 | 0 | 0 |
| 101002 | LP | Lab Collections | 12 † | 19 | 0 | 0 |
| 101005 | R | Informed Consent/Demographics | 0 | 3 | 0 | 0 |
| 101005 | R | HIV Test | 0 | 2 | 0 | 0 |
| 101005 | R | HLA Typing Sample | 2 † | 2 | 0 | 0 |
| 101005 | R | Biopsy | 1 † | 1 | 0 | 0 |
| 101005 | R | HPV Testing | 9 † | 5 | 0 | 0 |
| 101005 | R | Serum Cytokine Analysis | 12 † | 12 | 0 | 0 |
| 101005 | R | Lab Collections | 2 † | 20 | 0 | 0 |
| 101006 | LP | Informed Consent/Demographics | 0 | 3 | 0 | 0 |
| 101006 | LP | HIV Test | 0 | 2 | 0 | 0 |
| 101006 | LP | HLA Typing Sample | 3 † | 1 | 0 | 0 |
| 101006 | LP | Biopsy | 1 † | 1 | 0 | 0 |
| 101006 | LP | LEEP | 4 † | 0 | 0 | 0 |
| 101006 | LP | HPV Testing | 9 † | 5 | 0 | 0 |
| 101006 | LP | Serum Cytokine Analysis | 12 † | 12 | 0 | 0 |
| 101006 | LP | Lab Collections | 8 † | 20 | 0 | 1 |
| 101009 | R | Informed Consent/Demographics | 0 | 3 | 0 | 0 |
| 101009 | R | HIV Test | 0 | 2 | 0 | 0 |

LAB Reconciliation Report - eCRF Detail

Patient: 101006
eCRF: Lab Collections
Fields: Hematology Access. #, Hematology Collection Date, Serum Access. #, Serum Collection Date Select Visit(s): Check All | None

- ☑ Day -35  ☑ Day -33  ☑ Day 0  ☑ Wk 1 D1  ☑ Wk 2  ☑ Day 28
- ☑ Wk 6 D29  ☑ Wk 6  ☑ Wk 7  ☑ Day 56  ☑ Wk 8 D57  ☑ Wk 9
- ☑ Wk 10  ☑ Wk 13 D90  ☑ Wk 26 D180  ☑ Wk 52 D360  ☑ Unsched

[View Report]  [Reset]

Mismatch Only | Match Only | Both Mismatch and Match | *Inactive Items Only*

| Visit Name | Field | Answer CRF | Answer LAB | Action Taken | Comment | Active | Last Update | Updated By | |
|---|---|---|---|---|---|---|---|---|---|
| Wk 1 D1 | Serum Collection Date | 21 MAY 2010 08:01:00 | 21 JUN 2010 08:01:00 | ☐ | | ☐ | 1/25/2011 3:43:07 PM | Kati | Modify |

‡ Indicates a match as been found for this answer on the same visit.

AUTOMATED METHOD OF GENERATING RECONCILIATION REPORTS REGARDING MISMATCHES OF CLINICAL DATA RECEIVED FROM MULTIPLE SOURCES DURING A CLINICAL TRIAL

COPYRIGHT NOTICE AND AUTHORIZATION

Portions of the documentation in this patent document contain material that is subject to copyright protection. The copyright owner has no objection to the facsimile reproduction by anyone of the patent document or the patent disclosure as it appears in the Patent and Trademark Office file or records, but otherwise reserves all copyright rights whatsoever.

BACKGROUND OF THE INVENTION

Clinical trials are conducted to collect safety and efficacy data for new drugs or devices that a company wishes to make available to the public. A typical clinical trial for a new drug is performed by having a plurality of clinical research sites administer the drug to a plurality of patients who are screened and then enrolled at the respective sites. Each site is managed by a local site clinical investigator, who is typically a physician. A principal investigator or lead investigator is in charge of the clinical trial.

A clinical data management system (CDMS) is used to manage the data of a clinical trial. The clinical trial data includes patient data collected at the investigator sites in case report forms (CRFs), also, interchangeably referred to herein as "electronic case report forms" (eCRFs), and patient data received back from patient samples sent to labs. The patient data may also be received from an interactive voice response (IVR) system, or from diagnostic tests performed at the investigator sites, such as electrocardiogram (ECG) data.

During a clinical trial, patient data is collected from a plurality of different sources. In many instances, the same data is collected from more than one source. The data from one source sometimes does not match the same data from another source. When such mismatches occur, it is necessary to reconcile the data, which typically requires human intervention. The process of identifying the mismatches and tracking the mismatches to ensure that action is taken to reconcile them is an extremely complicated task. Attempts have been made in the prior art (discussed further below) to use spreadsheets and reports to perform this task. However, these prior art attempts are not efficient and thus have not provided an acceptable solution to this problem.

BRIEF SUMMARY OF THE INVENTION

An automated method is provided of generating a report of data collected from multiple sources during a clinical trial. The data includes a plurality of different data fields. A plurality of patients participate in the clinical trial. A first set of data obtained from case report forms associated with the patients is received at a processor. The case report forms are one source of data. A second set of data obtained from at least one source other than the case report forms is also received at the processor. At least some of the data in the first and second set of data include data associated with the same data fields. The processor identifies any mismatches in data associated with the same data fields in the first and second set of data. Mismatches associated with data fields obtained from the same case report forms are electronically grouped. A report is then generated of the data. The report shows the status of mismatches for each case report form or type of case report form.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. However, the invention is not limited to the precise arrangements and instrumentalities shown.

In the drawings:

FIGS. 1-3 are flowcharts in accordance with preferred embodiments of the present invention.

FIGS. 5-16 are user interface display screens in accordance with preferred embodiments of the present invention.

FIGS. 18-19 are additional user interface display screens in accordance with preferred embodiments of the present invention.

DETAILED DESCRIPTION OF THE INVENTION

Figure 2:
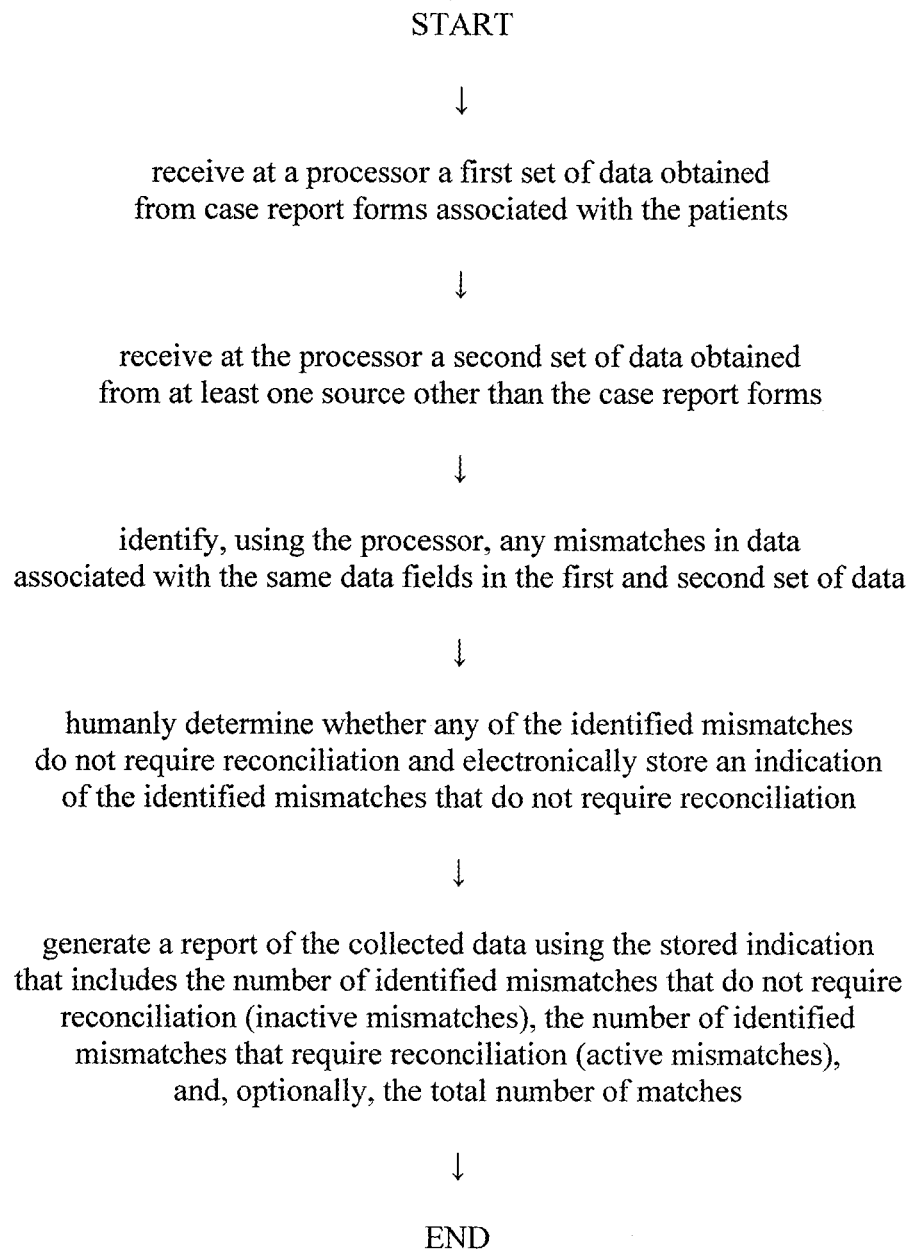

Certain terminology is used herein for convenience only and is not to be taken as a limitation on the present invention.

This patent application includes an Appendix having a file named appendix10001-50US.txt, created on Feb. 15, 2011, and having a size of 77,535 bytes. The Appendix is incorporated by reference into the present patent application. One preferred embodiment of the present invention is implemented via the source code in the Appendix. The Appendix is subject to the "Copyright Notice and Authorization" stated above.

The present invention is described in the context of features provided in a web-based commercially available product called The Single Interface™, marketed by Numoda Technologies, Inc. (Numoda), Philadelphia, Pa. In the present invention, Numoda functions as a service provider for hosting The Single Interface.

I. Overview

One preferred embodiment of the present invention provides an automated method of generating a report of data collected from multiple sources during a clinical trial. The data includes a plurality of different data fields. A plurality of patients participate in the clinical trial.

The method operates as follows:

1. A first set of data obtained from case report forms associated with the patients is received at a processor. The case report forms are one source of data.
2. A second set of data obtained from at least one source other than the case report forms is also received at the processor. At least some of the data in the first and second set of data include data associated with the same data fields. The second set of data may be obtained from entities that provide laboratory data for patients who are participating in the clinical trial or may be obtained from one or more electronic data sources, such as an IVR system.

3. The processor identifies any mismatches in data associated with the same data fields in the first and second set of data.
4. The processor electronically groups mismatches associated with data fields obtained from the same case report forms.
5. A report of the data is generated. The report shows the status of mismatches for each case report form or type of case report form. The status of the mismatches may include the total number of mismatches, and the number of mismatches where action has been taken to reconcile the mismatches. The status of mismatches for each case report form or type of case report form may be shown on a patient-by-patient basis (see bottom table of FIG. 7) or on a case report form basis (see upper table of FIGS. 7 and 13, and also FIG. 10).

The prior art spreadsheet process that was discussed above in the Background of the Invention section performed steps 1-3 and also generated various reports. Furthermore, the prior art spreadsheet process was capable of highlighting mismatches in data fields, counting the total number of mismatches, and allowed mismatches to be filtered by country, site, mismatches only, matches only, or both. It also included a memo (comment) field that allowed for human query entries. For example, a text entry could be made indicating what action was taken with respect to a mismatch. However, the prior art spreadsheet process did not electronically group mismatches associated with data fields obtained from the same case report forms (step 4), and thus did not generate the type of reports described in step 5.

This embodiment of the present invention may also include the following additional features:

a. The report in step 5 may further identify the number of case report forms that have at least one mismatch. See the "Task" column in selected figures. This column is a summary of individual patient eCFRs with at least one mismatch that does not have a check in the action taken checkbox for the selected filter criteria.

b. Step 4 may further include electronically grouping matches associated with data fields obtained from the same case report forms. If so, then step 5 would further include showing the status of the matches for each case report form or type of case report form. The status of the matches may be the total number of matches or the percentage of matches vs. mismatches.

FIG. 1 shows a self-explanatory flowchart of this embodiment.

Another preferred embodiment of the present invention provides an automated method of generating a report of data collected from multiple sources during a clinical trial. The data includes a plurality of different data fields. A plurality of patients participate in the clinical trial.

The method operates as follows:
1. A first set of data obtained from case report forms associated with the patients is received at a processor. The case report forms are one source of data.
2. A second set of data obtained from at least one source other than the case report forms is also received at the processor. At least some of the data in the first and second set of data include data associated with the same data fields.
3. The processor identifies any mismatches in data associated with the same data fields in the first and second set of data.
4. Humanly determine whether any of the identified mismatches do not require reconciliation and electronically store a field indication of the identified mismatches that do not require reconciliation.
5. Generate a report of the collected data. The report includes the number of identified mismatches that do not require reconciliation (referred to as "inactive mismatches") and the number of identified mismatches that require reconciliation (referred to as "active mismatches"). The report may also include the total number of matches.

The prior art spreadsheet process that was discussed above in the Background of the Invention section performed steps 1-3 and also generated various reports. It is also prior art that certain mismatches do not need to be reconciled. For example, mismatches associated with unscheduled visits do not need to be reconciled. The prior art process executed a separate program to locate such visits and created a separate report for the unscheduled visits. However, the prior art process had no process to store a field indication of the identified mismatches that do not require reconciliation (step 4), and then use that field indication to generate a report of the number of identified mismatches that do not require reconciliation (inactive mismatches) and the number of identified mismatches that require reconciliation (active mismatches), as described in step 5. This process provides an efficient way to flag inactive mismatches.

This embodiment of the present invention also allows for the mismatch status to be changed from inactive to active. More specifically, a human may determine during a subsequent review of the identified mismatches that do not require reconciliation that one or more of the identified mismatches that do not require reconciliation now require reconciliation. The previously stored field indication would then be deleted, and an updated report would then show such identified mismatches as mismatches that now require reconciliation.

FIG. 2 shows a self-explanatory flowchart of this embodiment.

Another preferred embodiment of the present invention provides an automated method of generating a report of data collected from multiple sources during a clinical trial. The data includes a plurality of different data fields. A plurality of patients participate in the clinical trial.

The method operates as follows:
1. A first set of data obtained from case report forms associated with the patients is received at a processor. The case report forms are one source of data.
2. A second set of data obtained from at least one source other than the case report forms is also received at the processor. At least some of the data in the first and second set of data include data associated with the same data fields.
3. The processor, in conjunction with human determination, identifies any mismatches in data associated with the same data fields in the first and second set of data that require reconciliation. (The human determination is required to remove inactive mismatches.)
4. Electronically store a field indication of the identified mismatches that have had an action taken to address the mismatch.
5. Generate a report of the collected data that includes the number of identified mismatches that require reconciliation and the number of identified mismatches that have had an action taken to address the mismatch.

As discussed above, the prior art spreadsheet process included a memo (comment) field that allowed for human query entries. For example, a text entry could be made indicating what action was taken with respect to a mismatch. However, the prior art process did not store a field indication of the identified mismatches that have had an action taken to address the mismatch (step 4), and thus could not generate the report in step 5 which includes the number of identified mismatches that have had an action taken to address the mismatch.

This embodiment of the present invention may also include the following additional features:

a. The report may further highlight the number of identified mismatches that require reconciliation if any one of the identified mismatches that require reconciliation has not had an action taken to address the mismatch. See the daggered numbers in the lower table in FIG. 7 and in the expanded view of the lower table in FIGS. 11 and 13.

b. The number of identified mismatches that require reconciliation is preferably included in an electronically selectable link that provides a detailed listing of the respective identified mismatches. In this manner, the report also provides a detailed report of the identified mismatches that require reconciliation. See, for example, FIG. 15 wherein "Mismatches Only" was selected by the filter.

FIG. 3 shows a self-explanatory flowchart of this embodiment.

Figure 4:
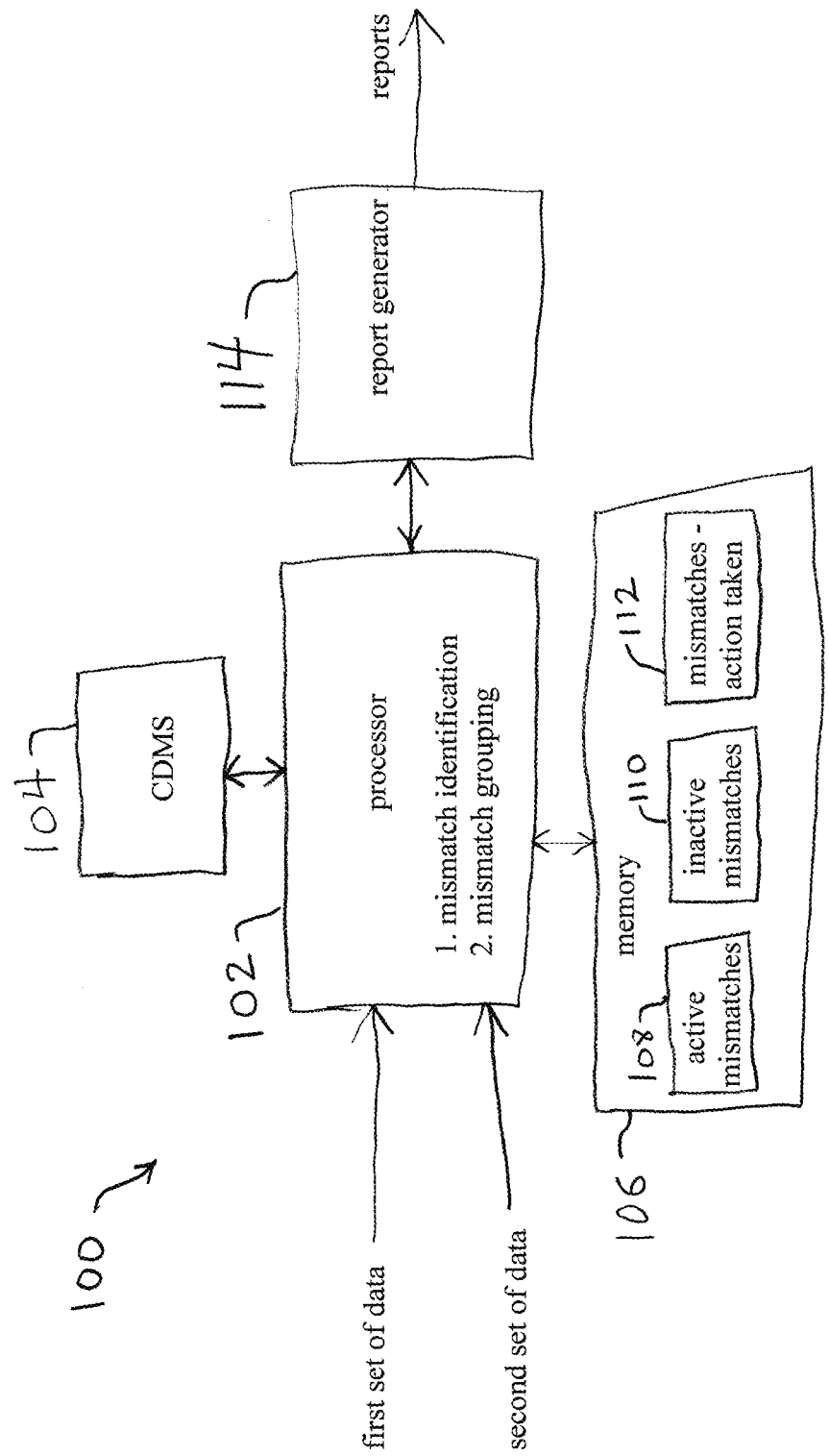
FIG. 4 is a schematic block diagram of a hardware system for implementing the preferred embodiments of the present invention.

FIG. 4 is a schematic block diagram of a hardware system 100 for implementing the embodiments disclosed above. The system 100 includes a processor 102, a CDMS 104, memory 106 and report generator 114. The processor 102 receives the first and second sets of data, which is also stored in the CDMS 104. The processor 102 performs the mismatch identification and mismatch grouping. The memory 106 stores data associated with the active mismatches 108, inactive mismatches 110, and mismatches that have had an action taken to address the mismatch 112. The report generator 114 generates the various reports described above.

Only two sources of data are shown in FIG. 1. However, there may be additional sources of data which may lead to additional potential mismatches if any two sources of data do not match.

II. Detailed Disclosure of One Preferred Embodiment
EDI Reconciliation Module Description (Electronic Data Integration)
Lab Reconciliation A clinic collects blood and urine samples from a clinical trial subject and records sample identification information (SII) which includes a patient identification number, the patient date of birth, the patient initials, the date and time of collection, an accession number and a visit identification number. Then the clinic sends the samples, along with the SII, out to an external lab for processing. Once the lab receives the samples and SII from the clinic, the lab manually enter the SII into their computer system. The lab tests are run on the collected blood and urine samples and the results are then entered into their computer system.

Within an agreed upon timeframe, typically once a week, the lab will export the SII, along with the lab test results, into a database table and then send that database table to a processor at Numoda. The processor at Numoda then compares the SII collected on the CRF at the clinic with the SII sent from the lab and must identify and resolve any mismatches. This process is important because oftentimes, due to human error, the SII is entered incorrectly at either the clinic or the lab and the FDA requires all of the data to match.

For a basic example of a mismatch, if according to the data in the Numoda clinical database, patient id 10001 had their blood and urine sample collected on Jan. 1, 2010, but according to the data sent from the lab, the blood and urine sample were collected on Jan. 11, 2010. In this example, the mismatched collection dates would need to be matched somehow. In order to resolve the mismatch, a query is generated by the Numoda data management team. Ultimately, the incorrect date will be identified and then corrected in either the Numoda clinical database or the lab database so that the collection dates in each database match.

To reconcile the data from one or more vendors, a computer program described herein performs at least the following functions:

1. Creates a summary report (FIG. 7, FIG. 8 and FIG. 13) of mismatched fields in two or more database tables with hyperlinks to a more detailed report (FIG. 15) for a field to field comparison. Additional details regarding these reports is provided below in the sections named "LAB Reconciliation Help" and "LAB Reconciliation—eCRF Detail Help.")

Figure 5:
Figure 6:
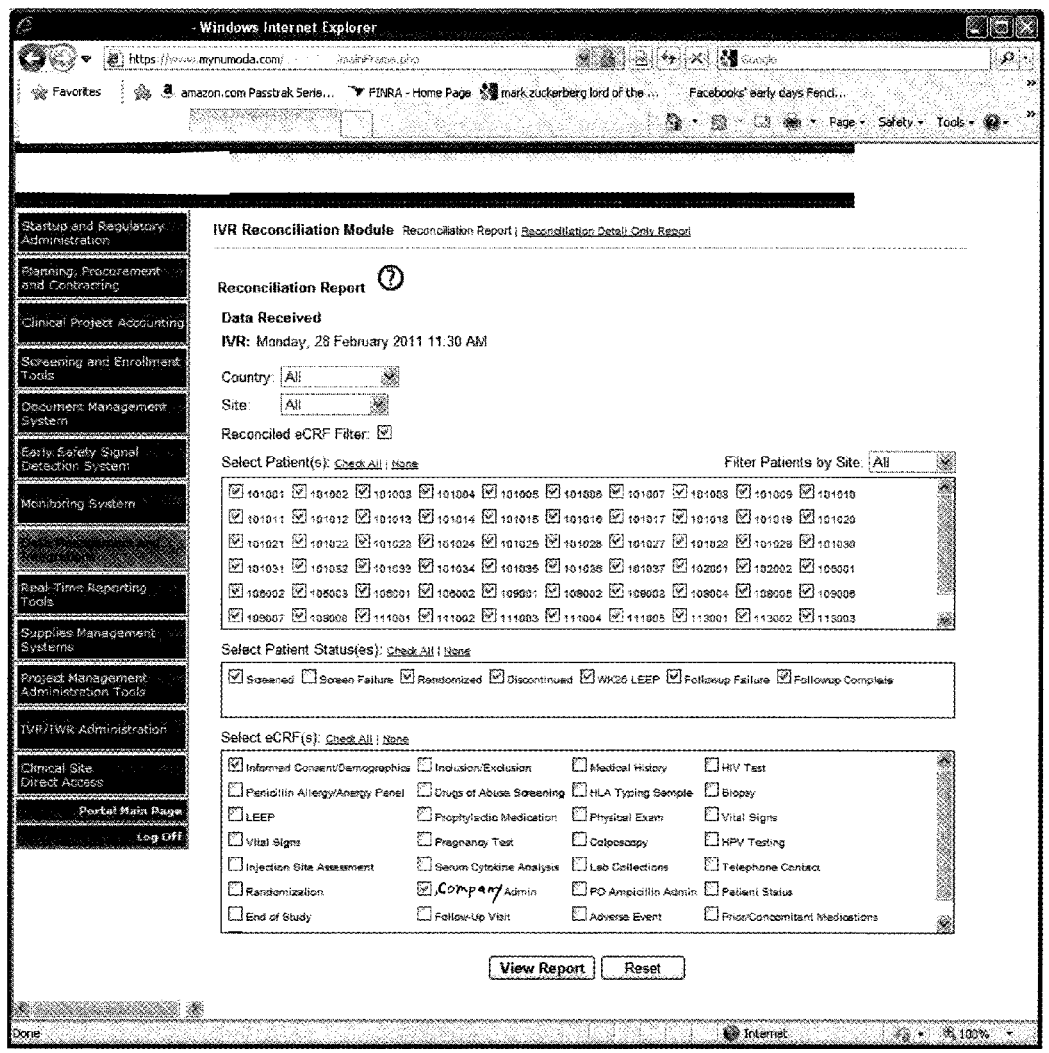

2. Makes trends in mismatched data easy to recognize with numerous report filtering options (FIG. 5 and FIG. 6) and allowing columns to be sorted (FIG. 7, FIG. 8, FIG. 11 and FIG. 13).

3. Organizes the mismatched fields into manageable subsets (CRFs). (FIG. 7, FIG. 8, FIG. 13 and FIG. 15).

4. Provides color indicators and tools to track employee actions taken to correct the mismatched fields. (FIG. 7, FIG. 8 FIG. 13 and FIG. 15). The color indicator is yellow highlighting (not shown) and displaying of a † (dagger) symbol.

Figure 13:
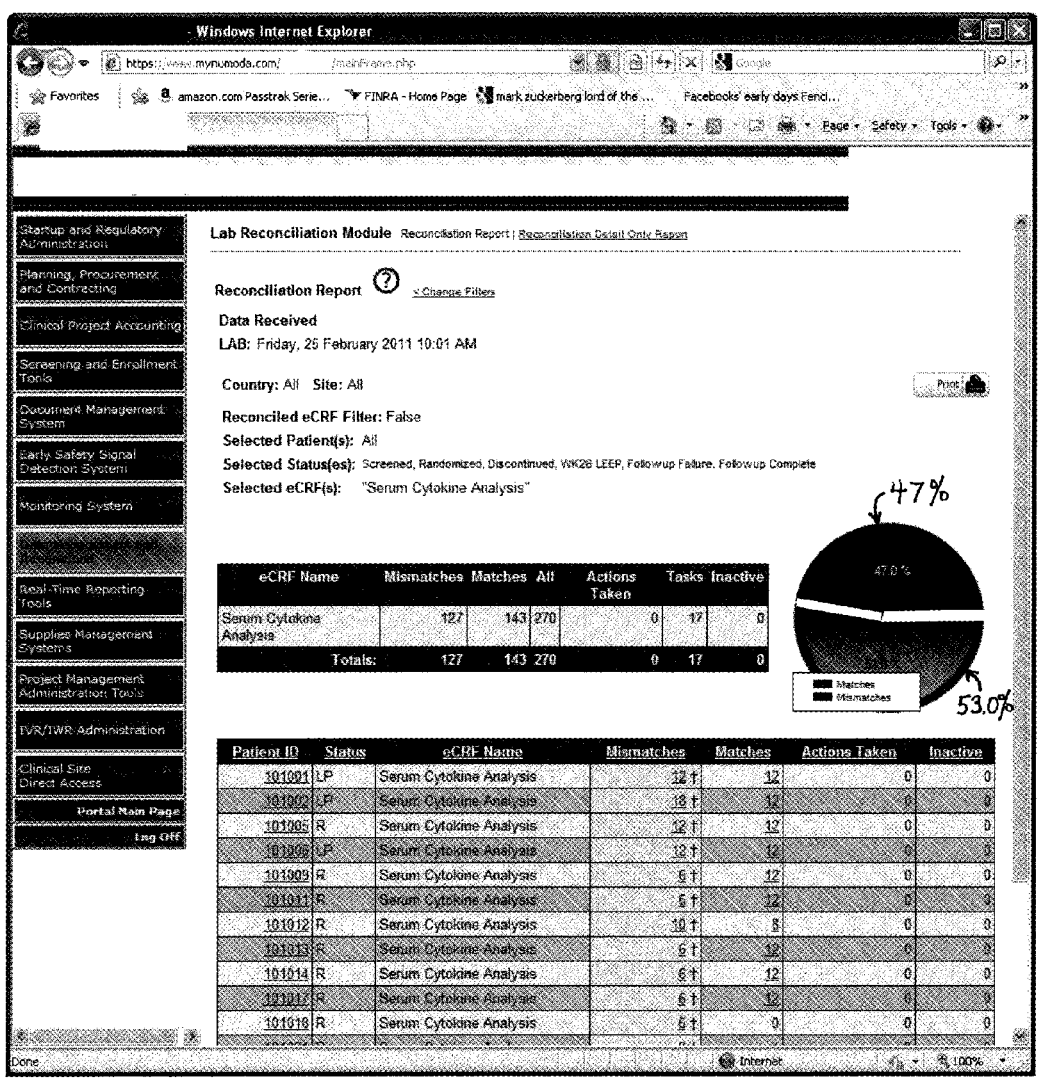

5. Verifies when mismatched fields become matched fields. (FIG. 7, FIG. 8 and FIG. 13)

6. Summarizes progress for the overall process and the user defined subsets (CRFs). (FIG. 7, FIG. 8 and FIG. 13)

7. Allows users to inactivate mismatches when the mismatch does not require reconciliation (FIG. 16—"Inactive Items Only" was selected by the filter).

Figure 7:
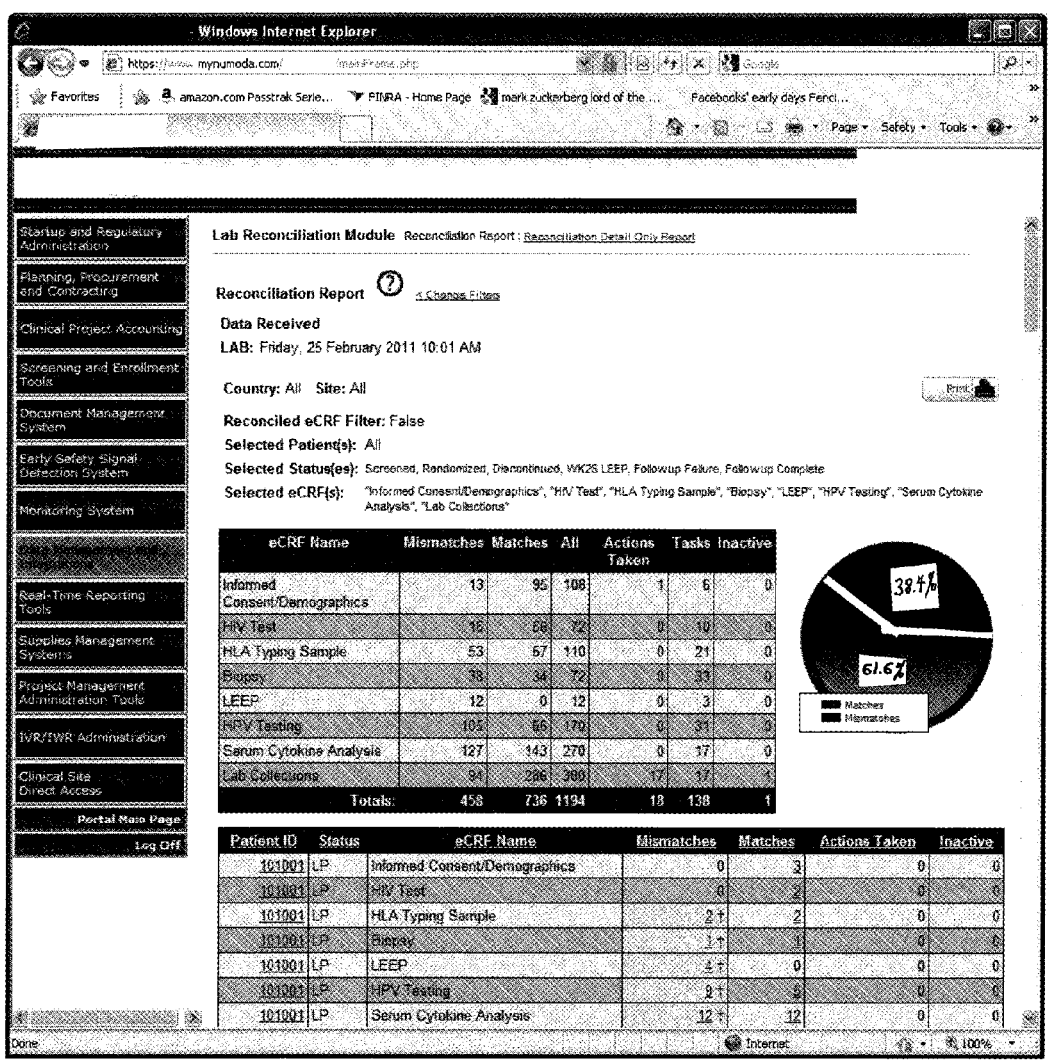
Figure 8:
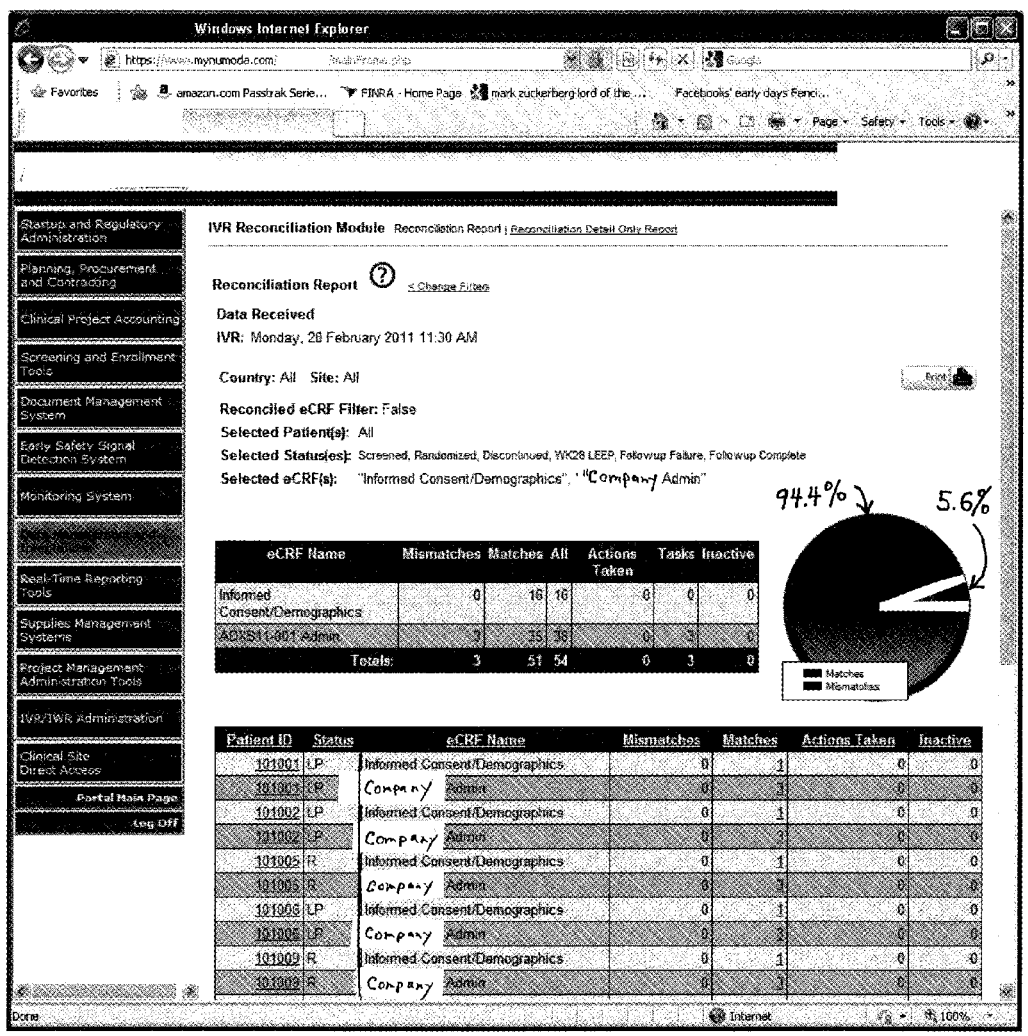
Figure 12:
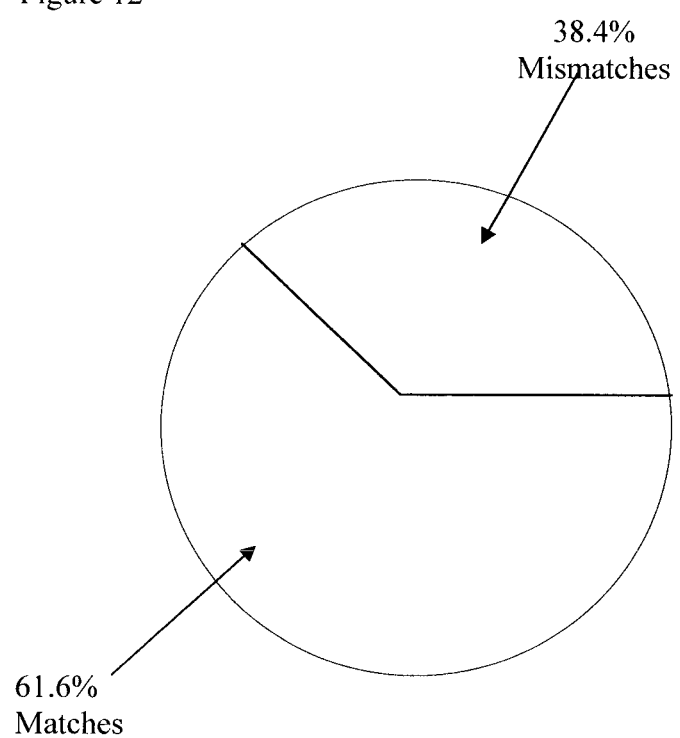

FIG. 10 shows an expanded view of the upper table in FIG. 7. FIG. 11 shows an expanded view of the lower table in FIG. 7. FIG. 12 shows an expanded view of the pie chart in FIG. 7.

Other key points of the computer program:

1. The program can be used to reconcile SII data from sources other than a Lab. For example, data from an IVR system or ECG data may be reconciled in a similar manner.

a. Example of ECG Reconciliation

A clinic uses an ECG machine during a patient visit and collects ECG result values and SII on a CRF while the machine sends data to the ECG company. Once the ECG company receives the ECG data, the company analyzes the values and stores the results and SII data in their computer system.

Within an agreed upon timeframe, typically once a week, the ECG company will export the SII, along with the ECG test results, into a database table and then send that database table to a processor at Numoda. The processor at Numoda then compares the SII collected at the clinic with the SII sent from the ECG company and must identify and resolve any mismatches. This process is important because oftentimes, due to human error, the SII is entered incorrectly at either the clinic or the ECG company. The FDA requires all of the data to match.

For a basic example of a mismatch, consider the following scenario: According to the data in the Numoda clinical database, patient id 10001 had their ECG done on Jan. 1, 2010, but according to the data sent from the ECG company, the ECG was performed on Jan. 11, 2010. In this example, the mismatched dates would need to be matched somehow. In order to resolve the mismatch, a query is generated by the Numoda data management team. Ultimately, the incorrect date will be identified and then corrected in either the Numoda clinical database or the ECG company database so that the dates in each database match.

b. An Interactive Voice Response (IVR) system collects patient data such as their initials and date of birth and assigns a specified study drug kit to the patient. The kit number and dispense or randomization date are recorded and the clinic gives the study drug kit to the patient. This sample identification information (SII) can include a patient identification number, the patient date of birth, the patient initials, the date and time of randomization and a kit number. The patient data is collected via telephone and stored in a specialized IVR database.

Using the IVR database, Numoda will compare the SII, along with the randomization date and kit number with the data collected at the clinic on CRFs. The processor at Numoda then compares the SIT collected with the IVR system with the data collected from the CRFs and must identify and resolve any mismatches. This process is important because oftentimes, due to human error, the SII is entered incorrectly using either the phone or the CRF. The FDA requires all of the data to match.

For a basic example of a mismatch, consider the following scenario: According to the data in the Numoda clinical database, patient id 10001 had their randomization completed on Jan. 1, 2010, but according to the data sent from the IVR, the randomization was completed on Jan. 11, 2010. In this example, the mismatched randomization dates would need to be matched somehow. In order to resolve the mismatch, a query is generated by the Numoda data management team. Ultimately, the incorrect date will be identified and then corrected in either the Numoda clinical database or the IVR database so that the collection dates in each database match.

2. The program can be used to reconcile data from multiple labs. (FIG. 9)

Figure 14:
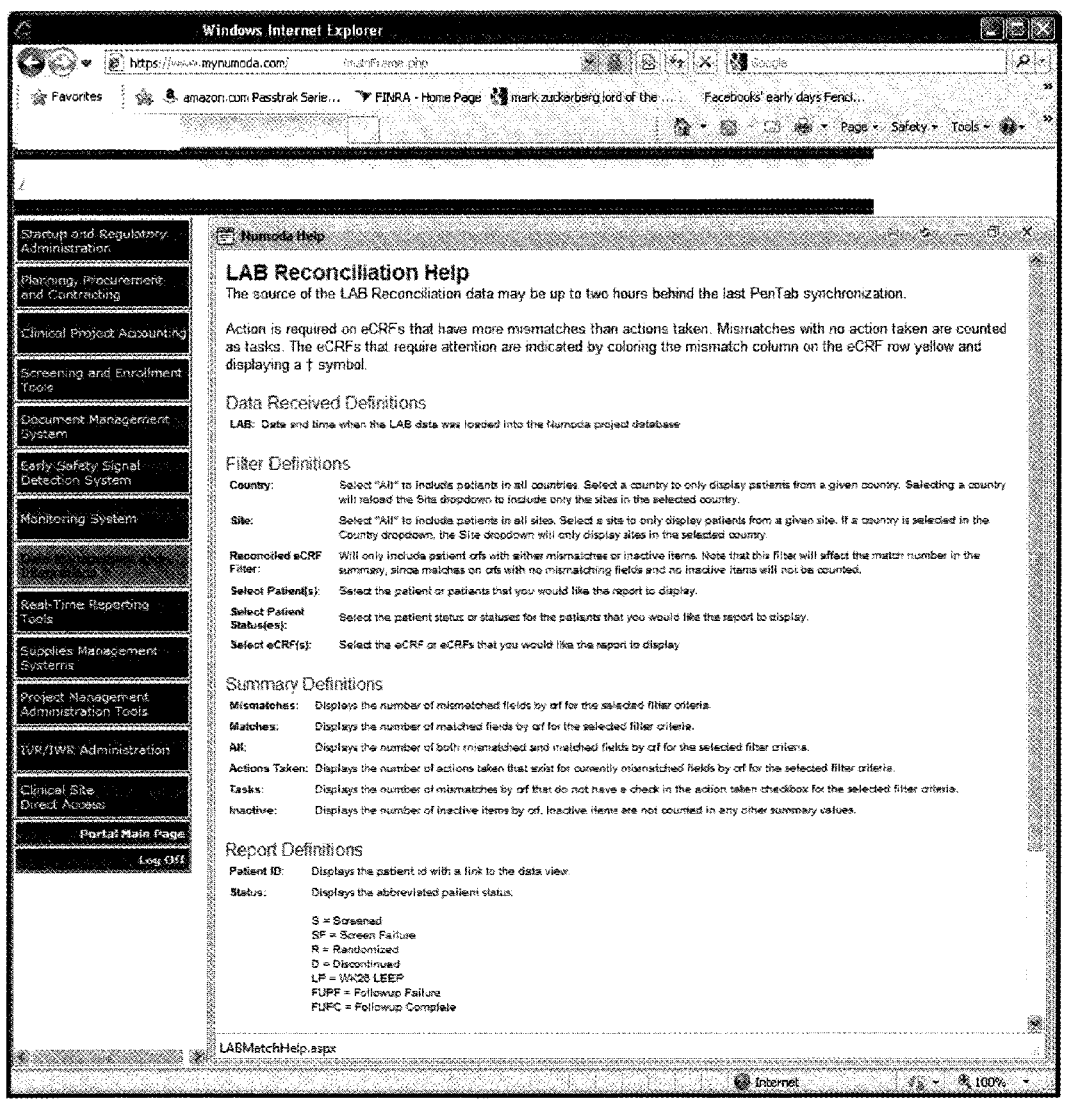

LAB Reconciliation Help (FIG. 14 Shows an Excerpt of the Help Screen)

The source of the LAB Reconciliation data may be up to two hours behind the last PenTab synchronization.

Action is required on eCRFs that have more mismatches than actions taken. Mismatches with no action taken are counted as tasks. The eCRFs that require attention are indicated by coloring the mismatch column on the eCRF row highlighted in yellow (not shown) and displaying a † symbol.

Data Received Definitions

LAB: Date and time when the LAB data was loaded into the Numoda project database.

Filter Definitions

Country: Select "All" to include patients in all countries. Select a country to only display patients from a given country. Selecting a country will reload the Site dropdown to include only the sites in the selected country.

Site: Select "All" to include patients in all sites. Select a site to only display patients from a given site. If a country is selected in the Country dropdown, the Site dropdown will only display sites in the selected country.

Reconciled eCRF Filter: Will only include patient CRFs with either mismatches or inactive items. Note that this filter will affect the match number in the summary, since matches on CRFs with no mismatching fields and no inactive items will not be counted.

Select Patient(s): Select the patient or patients that you would like the report to display.

Select Patient Status(es): Select the patient status or statuses for the patients that you would like the report to display.

Select eCRF(s): Select the eCRF or eCRFs that you would like the report to display.

SUMMARY DEFINITIONS

Mismatches: Displays the number of mismatched fields by CRF for the selected filter criteria.

Matches: Displays the number of matched fields by CRF for the selected filter criteria.

All: Displays the number of both mismatched and matched fields by CRF for the selected filter criteria.

Actions Taken: Displays the number of actions taken that exist for currently mismatched fields by CRF for the selected filter criteria.

Tasks: Displays the number of patient CRFs with at least one mismatch that do not have a check in the action taken checkbox for the selected filter criteria.

Inactive: Displays the number of inactive items by CRF. Inactive items are not counted in any other summary values.

Report Definitions

Patient ID: Displays the patient id with a link to the data view.

Status: Displays the abbreviated patient status:
   S=Screened
   SF=Screen Failure
   R=Randomized
   D=Discontinued
   LP=WK26 LEEP
   FUPF=Followup Failure
   FUPC=Followup Complete Some of these statuses are specific to the particular study being conducted.

eCRF Name: Displays the eCRF name.

Mismatches: Displays the number of mismatched fields by patient CRF for the selected filter criteria. The link goes to the eCRF Detail page with the "Mismatch Only" filter pre-selected.

Matches: Displays the number of matched fields by patient CRF for the selected filter criteria. The link goes to the eCRF Detail page with the "Match Only" filter pre-selected.

Actions Taken: Displays the number of actions taken for currently mismatched fields by patient CRF for the selected filter criteria. The link goes to the eCRF Detail page with the "Both Mismatch and Match" filter pre-selected.

Inactive: Displays the number of inactive items by patient CRF for the selected filter criteria. The link goes to the eCRF Detail page with the "Inactive Items Only" filter pre-selected.

LAB Reconciliation—eCRF Detail Help

The source of the LAB Reconciliation—eCRF Detail data may be up to two hours behind the last PenTab synchronization.

Action should be taken to resolve mismatches. Typically, mismatches are resolved by generating queries from the Data View. When all the queries for a given mismatch have been created, the action taken checkbox should be checked.

Header Definitions

Patient: Displays the patient id of the patient shown on this detail page with a link to their Data View.

eCRF: Displays the name of the eCRF being shown on this detail page.

Fields: Displays the names of the fields or questions being compared on this detail page.

Filter Definitions
Visit(s): Select the visit or visits that you would like the report to display.
Mismatch and Match Toggle Definitions
Mismatch Only: Click this link to display mismatches only.
Match Only: Click this link to display matches only.
Both Mismatch and Match: Click this link to display both mismatches and matches.
Inactive Items Only: Click this link to display inactive items.
Report Definitions
Visit Name: Displays the visit name for the visit that the eCRF data was collected on.
Field: Displays the field name or question that was asked on the eCRF to collect the data being compared.
Answer CRF: Displays the answer collected at the site or clinic that is being stored in Numoda's database.
Answer LAB: Displays the answer entered by the LAB vendor into their database.
Action Taken: When all the queries for a given mismatch have been created, the action taken checkbox should be checked.
Comment: Enter any comments relevant to the mismatch.
Active: The Active checkbox is used for removing items from the reconciliation report totals. Inactive items will not be counted as mismatches, matches or tasks. Inactive items can be viewed and reactivated by clicking on the "Inactive Items Only" toggle.
Last Update: Displays the date that the item was modified.
Updated By: Displays the full name of the user who last modified the item.
Modify Button: Use this button to modify the item.

Figure 18:
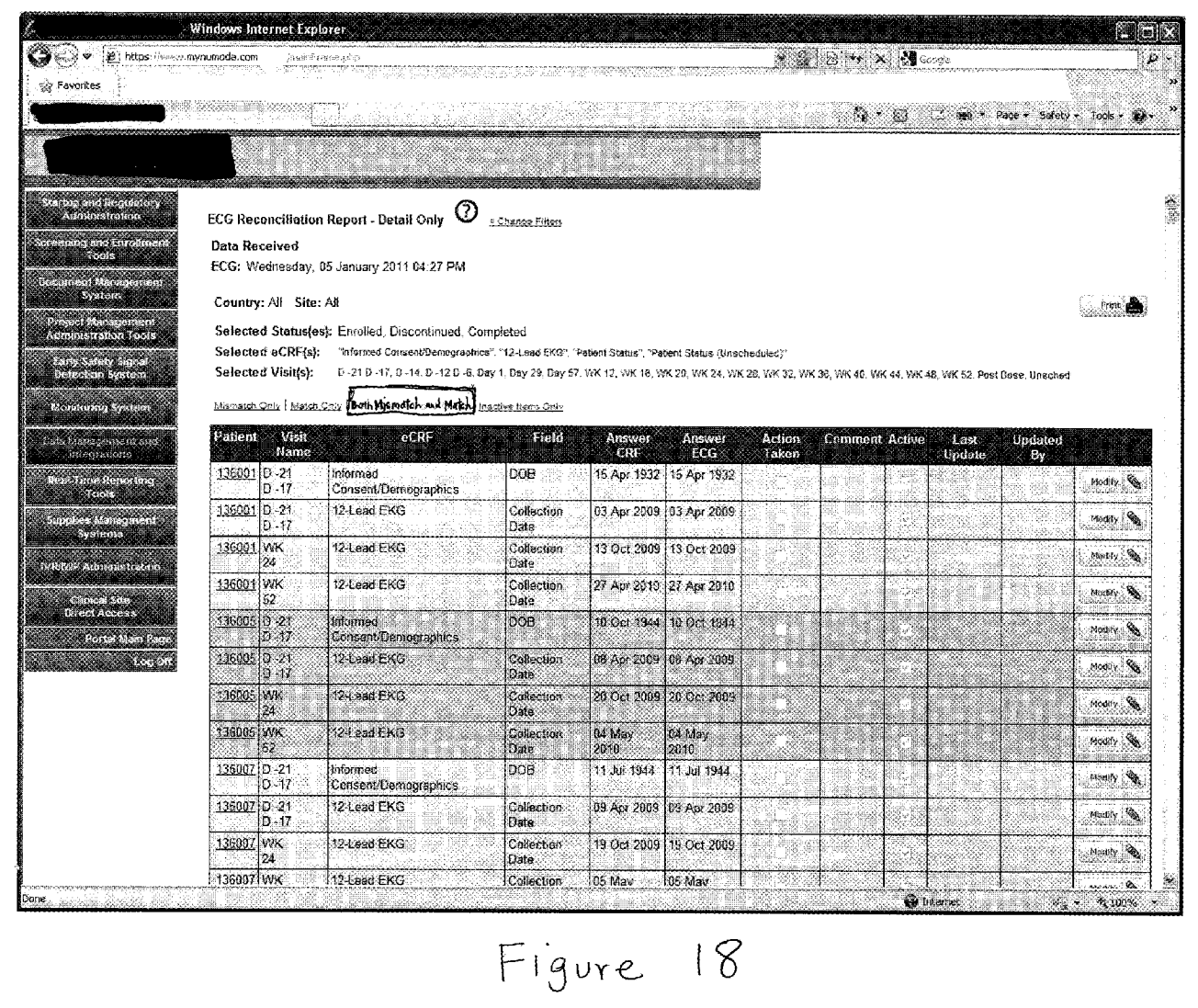
Figure 19:
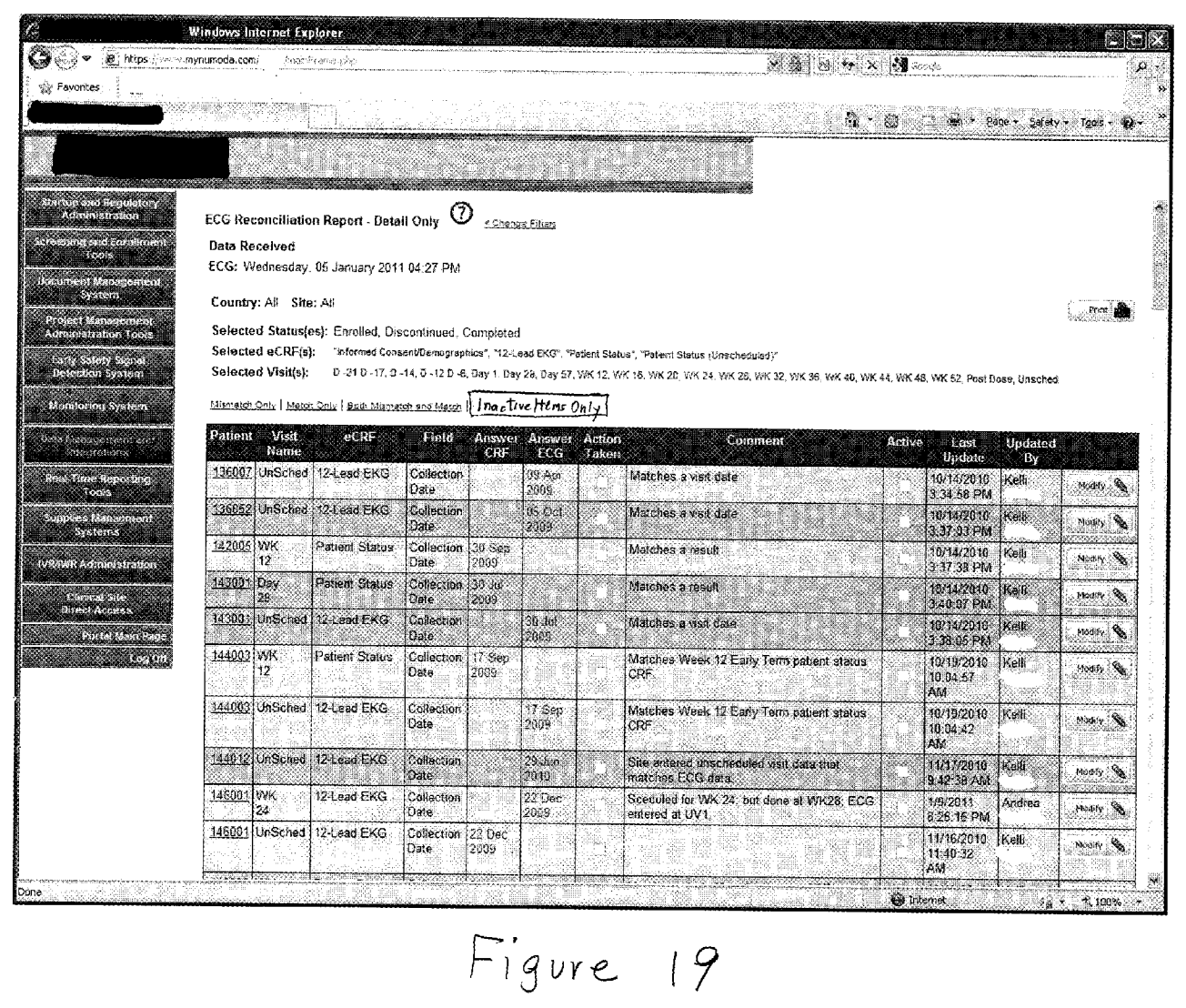

The lower table of FIG. 7 shows that all CRFs of the same type for each patient are grouped together. However, in an alternative embodiment, individual CRFs may be shown in the report, which can be referred to as a detail only report. FIGS. 18 and 19 show examples of detail only reports. These reports are most useful when there is not a very large amount of data being reconciled since it allows the user to see all of the data for all of the CRFs being compared, all at the same time. FIG. 19 further illustrates the use of the inactive feature to exclude mismatches that do not require reconciliation. In FIG. 19, "Inactive Items Only" was selected by the filter. In FIG. 18, "Both Mismatch and Match" were selected by the filter.

Figure 17:
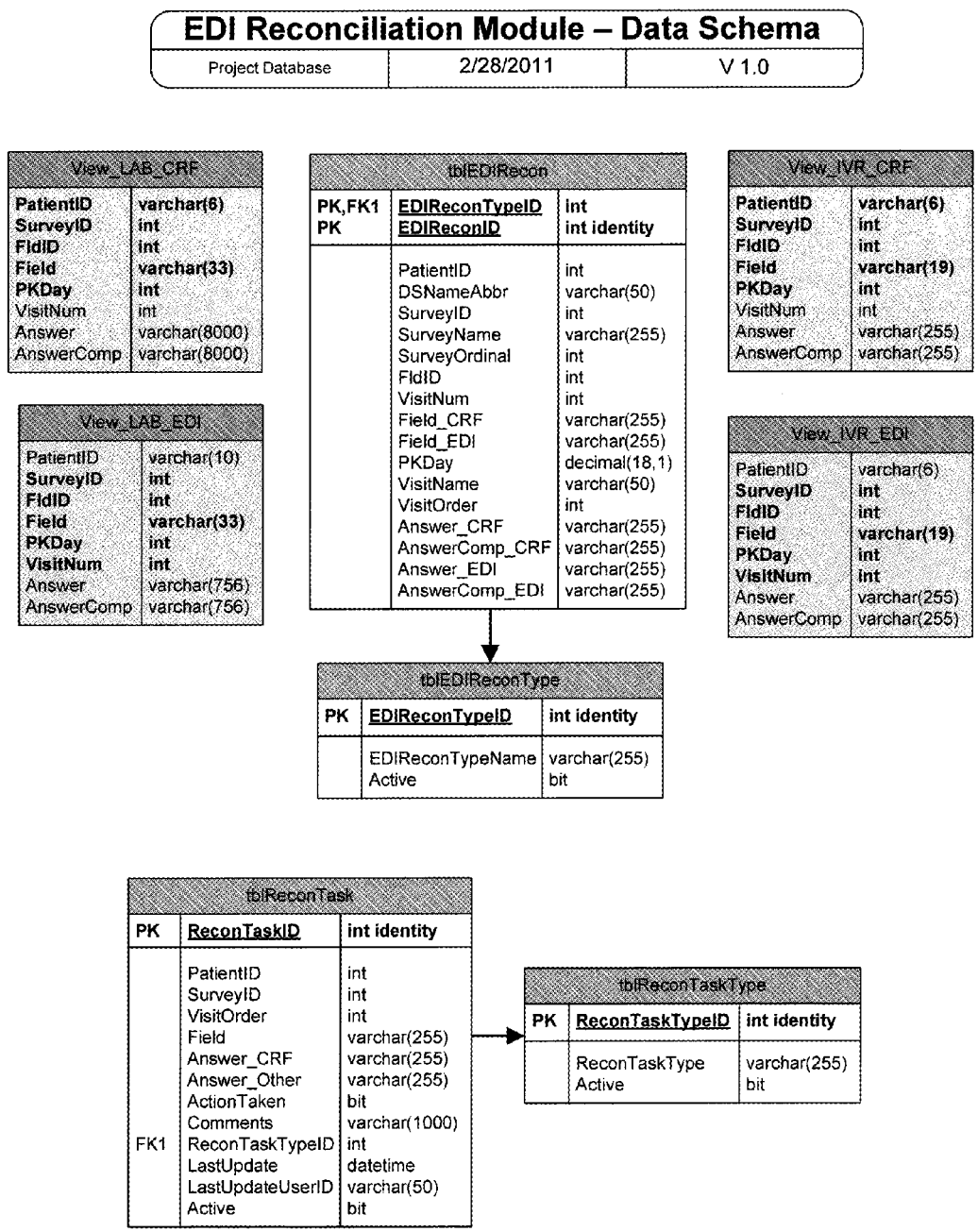
FIG. 17 is a data schema associated with one preferred embodiment of the present invention.

FIG. 17 is a data schema associated with one preferred embodiment of the present invention, as implemented via the source code in the Appendix. The embodiment implemented via the source code in the Appendix refers to the embodiment shown in FIGS. 5-16.

The present invention may be implemented with any combination of hardware and software. If implemented as a computer-implemented apparatus, the present invention is implemented using means for performing all of the steps and functions described above.

When implemented in software, the software code can be executed on any suitable processor or collection of processors, whether provided in a single computer or distributed among multiple computers.

The present invention can also be included in an article of manufacture (e.g., one or more computer program products) having, for instance, computer readable storage media. The storage media has computer readable program code stored therein that is encoded with instructions for execution by a processor for providing and facilitating the mechanisms of the present invention. The article of manufacture can be included as part of a computer system or sold separately.

The storage media can be any known media, such as computer memory, one or more floppy discs, compact discs, optical discs, magnetic tapes, flash memories, circuit configurations in Field Programmable Gate Arrays or other semiconductor devices, or other tangible computer storage medium. The storage media can be transportable, such that the program or programs stored thereon can be loaded onto one or more different computers or other processors to implement various aspects of the present invention as discussed above.

The computer used herein may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable, mobile, or fixed electronic device.

The computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

The terms "program" or "software" are used herein in a generic sense to refer to any type of computer code or set of computer-executable instructions that can be employed to program a computer or other processor to implement various aspects of the present invention as discussed above. The computer program need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, and the like, that perform particular tasks or implement particular abstract data types. The functionality of the program modules may be combined or distributed as desired in various embodiments.

Data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Preferred embodiments of the present invention may be implemented as methods, of which examples have been provided. The acts performed as part of the methods may be ordered in any suitable way. Accordingly, embodiments may be constructed in which acts are performed in an order different than illustrated, which may include performing some acts simultaneously, even though such acts are shown as being sequentially performed in illustrative embodiments.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention.

What is claimed is:

1. An automated method of generating a report of data collected from multiple sources during a clinical trial, the data including a plurality of different data fields, wherein a plurality of patients participate in the clinical trial, the method comprising:
   (a) receiving at a processor a first set of data obtained from case report forms associated with the patients, the case report forms being one source of data, wherein
      (i) each of the case report forms has a subject name that is used to identify the case report forms,
      (ii) there are a plurality of case report forms which have different subject names, and
      (iii) at least some of the case report forms which have different subject names include a different subset of data fields;
   (b) receiving at the processor a second set of data obtained from at least one source other than the case report forms, wherein at least some of the data in the first and second set of data include data associated with the same data fields;
   (c) identifying, using the processor, any mismatches in data associated with the same data fields in the first and second set of data;
   (d) electronically grouping, using the processor, mismatches associated with data fields obtained from the same case report forms; and
   (e) generating a report of the data, the report showing the status of mismatches for each case report form or type of case report form.

2. The method of claim 1 wherein step (d) further includes electronically grouping matches associated with data fields obtained from the same case report forms, and wherein step (e) further includes showing the status of the matches for each case report form or type of case report form.

3. The method of claim 2 wherein the status of the matches includes the total number of matches.

4. The method of claim 3 wherein the report further shows the percentage of matches versus mismatches.

5. The method of claim 1 wherein the status of the mismatches includes the total number of mismatches.

6. The method of claim 5 wherein the status of the mismatches includes the number of mismatches where action has been taken to reconcile the mismatch.

7. The method of claim 1 wherein the report shows the status of mismatches for each case report form or type of case report form on a case report form type basis.

8. The method of claim 7 wherein step (e) further includes identifying the number of case report forms that have at least one mismatch.

9. The method of claim 1 wherein the report shows the status of mismatches for each case report form or type of case report form on a patient-by-patient basis.

10. The method of claim 1 wherein the second set of data is obtained from entities that provide laboratory data for patients who are participating in the clinical trial.

11. The method of claim 1 wherein the second set of data is obtained from one or more electronic data sources.

12. A computer program product for generating a report of data collected from multiple sources during a clinical trial, the data including a plurality of different data fields, wherein a plurality of patients participate in the clinical trial, the computer program product comprising non-transitory, tangible computer-readable storage media encoded with instructions for execution by a processor to perform a method comprising:
   (a) receiving at the processor a first set of data obtained from case report forms associated with the patients, the case report forms being one source of data, wherein
      (i) each of the case report forms has a subject name that is used to identify the case report forms,
      (ii) there are a plurality of case report forms which have different subject names, and (iii) at least some of the case report forms which have different subject names include a different subset of data fields;
   (b) receiving at the processor a second set of data obtained from at least one source other than the case report forms, wherein at least some of the data in the first and second set of data include data associated with the same data fields;
   (c) identifying, using the processor, any mismatches in data associated with the same data fields in the first and second set of data;
   (d) electronically grouping, using the processor, mismatches associated with data fields obtained from the same case report forms; and
   (e) generating a report of the data, the report showing the status of mismatches for each case report form or type of case report form.

13. The computer program product of claim 12 wherein step (d) further includes electronically grouping matches associated with data fields obtained from the same case report forms, and wherein step (e) further includes showing the status of the matches for each case report form or type of case report form.

14. The computer program product of claim 13 wherein the status of the matches includes the total number of matches.

15. The computer program product of claim 14 wherein the report further shows the percentage of matches versus mismatches.

16. The computer program product of claim 12 wherein the status of the mismatches includes the total number of mismatches.

17. The computer program product of claim 16 wherein the status of the mismatches includes the number of mismatches where action has been taken to reconcile the mismatch.

18. The computer program product of claim 12 wherein the report shows the status of mismatches for each case report form or type of case report form on a case report form type basis.

19. The computer program product of claim 18 wherein step (e) further includes identifying the number of case report forms that have at least one mismatch.

20. The computer program product of claim 12 wherein the report shows the status of mismatches for each case report form or type of case report form on a patient-by-patient basis.

21. The computer program product of claim 12 wherein the second set of data is obtained from entities that provide laboratory data for patients who are participating in the clinical trial.

22. The computer program product of claim 12 wherein the second set of data is obtained from one or more electronic data sources.

* * * * *